(12) United States Patent
Thanigachalam et al.

(10) Patent No.: US 8,359,902 B2
(45) Date of Patent: Jan. 29, 2013

(54) GAS SENSOR APPARATUS FOR AUTOMOTIVE EXHAUST GAS APPLICATIONS

(75) Inventors: Palani Thanigachalam, Bangalore (IN); Thirumani A. Selvan, Bangalore (IN)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 12/870,649

(22) Filed: Aug. 27, 2010

(65) Prior Publication Data

US 2010/0314249 A1 Dec. 16, 2010

Related U.S. Application Data

(63) Continuation of application No. 11/710,068, filed on Feb. 23, 2007, now abandoned.

(51) Int. Cl.
*G01N 27/12* (2006.01)
(52) U.S. Cl. ...................................... 73/23.31; 73/31.05
(58) Field of Classification Search .................. 73/1.89; 29/593
See application file for complete search history.

(56) References Cited

U.S. PATENT DOCUMENTS

| | | | |
|---|---|---|---|
| 3,886,785 A | 6/1975 | Stadler et al. | |
| 3,911,386 A | 10/1975 | Beaudoin et al. | |
| 3,928,161 A * | 12/1975 | McIntyre et al. | 204/428 |
| 3,936,794 A | 2/1976 | Beaudoin et al. | |
| 3,940,327 A * | 2/1976 | Wagner et al. | 204/428 |
| 4,040,930 A | 8/1977 | Dillon | |
| 4,130,797 A | 12/1978 | Hattori et al. | |
| 4,277,323 A | 7/1981 | Muller et al. | |
| 4,282,080 A | 8/1981 | Muller et al. | |
| 4,283,261 A | 8/1981 | Maurer et al. | |
| 4,300,990 A | 11/1981 | Maurer | |
| 4,305,903 A | 12/1981 | Krause | |
| 4,310,401 A | 1/1982 | Stahl | |
| 4,413,502 A | 11/1983 | Ohta et al. | |
| 4,414,531 A | 11/1983 | Novak | |
| 4,419,212 A | 12/1983 | Dietz et al. | |
| 4,437,971 A | 3/1984 | Csanitz et al. | |
| 4,489,596 A | 12/1984 | Linder et al. | |
| 4,535,316 A | 8/1985 | Wertheimer et al. | |
| 4,556,475 A | 12/1985 | Bayha et al. | |
| 4,560,463 A | 12/1985 | Frey et al. | |
| 4,609,454 A | 9/1986 | Ziegler | |
| 4,636,293 A | 1/1987 | Bayha et al. | |
| 4,756,885 A | 7/1988 | Raff et al. | |
| 5,246,562 A | 9/1993 | Weyl et al. | |
| 5,942,092 A * | 8/1999 | Weyl et al. | 204/424 |
| 5,955,656 A | 9/1999 | Graser et al. | |
| 6,018,982 A | 2/2000 | Friese et al. | |
| 6,164,120 A | 12/2000 | Friese et al. | |
| 6,206,377 B1 | 3/2001 | Weyl | |

(Continued)

FOREIGN PATENT DOCUMENTS

| | | |
|---|---|---|
| EP | 0936461 | 8/1999 |
| GB | 1467735 | 3/1977 |

*Primary Examiner* — Daniel Larkin
(74) *Attorney, Agent, or Firm* — Seager Tufte & Wickhem LLC

(57) ABSTRACT

A gas sensor apparatus and method of forming the same generally includes a gas sensor element comprising a heater and a plurality of electrodes. A ceramic substrate can be provided for supporting the electrodes on one side of the ceramic substrate and the heater on the opposite side of the ceramic substrate. The gas sensor element is preferably embedded in the ceramic substrate. The ceramic substrate also possesses a substantially circular shape in order to prevent a breakage of the gas sensor element, avoid thermal loss, and permit the gas sensor apparatus to withstand mechanical shock and high vibrations while occupying a minimal package space.

15 Claims, 9 Drawing Sheets

U.S. PATENT DOCUMENTS

| | | |
|---|---|---|
| 6,223,583 B1 | 5/2001 | Friese et al. |
| 6,257,573 B1 | 7/2001 | Munoz et al. |
| 6,273,432 B1 | 8/2001 | Weyl et al. |
| 6,311,453 B1 | 11/2001 | Mechnick |
| 6,319,376 B1 | 11/2001 | Graser et al. |
| 6,344,134 B1 | 2/2002 | Yamada et al. |
| 6,347,543 B1 | 2/2002 | Geier et al. |
| 6,352,632 B1 | 3/2002 | Inagaki et al. |
| 6,375,828 B2 | 4/2002 | Ando et al. |
| 6,408,680 B2 | 6/2002 | Friese et al. |
| 6,474,655 B1 | 11/2002 | Weyl et al. |
| 6,487,890 B1 | 12/2002 | Weyl et al. |
| 6,585,872 B2 | 7/2003 | Donelon et al. |
| 6,613,206 B1 | 9/2003 | Weyl et al. |
| 6,672,132 B1 | 1/2004 | Weyl et al. |
| 6,672,900 B2 | 1/2004 | France et al. |
| 7,021,354 B2 | 4/2006 | Kobayashi et al. |
| 7,159,447 B2 | 1/2007 | Nakagawa |
| 2004/0159547 A1 | 8/2004 | Haraguchi et al. |
| 2008/0206107 A1 | 8/2008 | Thanigachalam et al. |

\* cited by examiner

GAS SENSOR APPARATUS FOR AUTOMOTIVE EXHAUST GAS APPLICATIONS

PRIORITY

This application is a continuation of U.S. patent application Ser. No. 11/710,068, filed Feb. 23, 2007, now abandoned, entitled "GAS SENSOR APPARATUS FOR AUTOMOTIVE EXHAUST GAS APPLICATIONS", which is incorporated herein by reference.

TECHNICAL FIELD

Embodiments are generally related to sensor methods and systems. Embodiments are also related to gas sensors. Embodiments are additionally related to gas sensor packaging devices, systems and methods of forming the same.

BACKGROUND

Sensors are often utilized in association with internal combustion engines to measure operating parameters and constituents of a resulting feed stream. For example, an exhaust gas sensor in a control system of an internal combustion engine can be used to measure the parameter of air/fuel ratio, CO, $CO_2$, $NO_x$, etc. It is important to determine the gas concentration of exhaust gas in order to control the emission of an automotive engine. A control system can then use this information to control the engine parameters and thereby allow for minimum emissions.

An engine controller can then employ the air/fuel ratio information to control the feed stream that flows through the engine and into an after treatment device, such as a catalytic converter. A properly controlled gas feed stream is important for the complete operation of the exhaust after treatment and during light-off and steady-state warmed-up operations of the utilized control system.

Construction of a current sensor element can take place in the context of a planar-type (e.g., thin and long ceramic) substrate, which protrudes externally from the gas sensor housing for measuring gas concentration. Since the configuration is planar and thinner, the possibility of breakage due to vibration and mechanical shock is very high It is known that the control of burning associated with an internal combustion engine is a function of the concentration of air-fuel ratio contained in exhaust gases. The concentration of the $NO_x$ and the air-fuel ratio is effective in providing energy savings and emission control capabilities. In gas sensor configurations suitable for measuring the concentration of oxygen or other gases like CO, NOx, CO2, etc., in exhaust gases, a solid electrolyte body constructed from zirconia or metal oxide semiconductor (MOS) based gas sensors can be utilized. This type of gas sensor, however, in order to be effective, must be reduced in size, while maintaining efficient production costs and improving its durability and reliability. These factors are difficult to achieve.

In order to sense gas concentration, such as O2, NOx etc., a gas sensor element should be operated at high temperature. For example, a zirconia sensor for measuring oxygen, should be maintained at 650 deg C. An electric power circuit controls the temperature of the sensor element. Designing the sensor element with small size is important in order to reduce power required to maintain the sensor at this temperature.

It is believed that a solution to overcoming these problems involves the implementation of an improved sensor apparatus, which can be efficiently fabricated at a low cost for automotive exhaust gas applications.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved gas sensor apparatus and method.

It is another aspect of the present invention to provide for a gas sensor apparatus that avoids breakage of the utilized sensor element.

It is another aspect of the present invention to provide for a gas sensor packaging apparatus in which thermal loss is minimized.

It is further aspect of the present invention to provide for a gas sensor apparatus that operates with a reduced operating power.

The aforementioned aspects and other objectives and advantages can now be achieved as described herein. A gas sensor apparatus and method of forming the same are disclosed herein. The gas sensor apparatus generally includes a gas sensor element comprising a heater and a plurality of electrodes. Additionally, a ceramic substrate can be provided for supporting the plurality of electrodes on one side of the ceramic substrate and the heater on an opposite side of the ceramic substrate. The gas sensor element is preferably embedded in the ceramic substrate. The ceramic substrate also possesses a substantially circular shape in order to prevent a breakage of the gas sensor element, avoid thermal loss, and permit the gas sensor apparatus to withstand mechanical shock and high vibrations while occupying a minimal packaging space.

The gas sensor apparatus also includes a plurality of contact terminals connected to the ceramic substrate in order to provide at least one electrical connection to the gas sensor apparatus. A metallic housing can also be provided, which surrounds and protects the gas sensor element, the heater element and the ceramic substrate. The gas the sensor element additionally includes a holding end portion located and secured in the metallic housing and a sensing end portion exposed to exhaust gases thereof. The heater can be provided in the form of a plurality of platinum heater elements, while electrodes are preferably formed from platinum. The sensing side of the substrate can include two platinum electrodes over which a sensing material can be coated, such as metal oxide semiconductor (MOS), or upon which a zirconia element can be attached.

The gas sensor element also includes at least one platinum conductive pad. The plurality of contact terminals can be resistance-welded to the ceramic substrate. The heater also maintains the temperature of the gas sensor element. Additionally, the metallic housing can be configured to include an outer baffle and an inner baffle provided in the metallic housing, thereby covering a gas exposed portion of the gas sensor element. The inner baffle forms a cup-like groove towards the gas sensor element. Additionally, an embossed feature can be provided, which assists a flow of gas flow near the gas sensor element.

The disclosed gas sensor apparatus is based on an innovative packaging design that avoid breakage of the sensor element, while the substrate shape can be circular with one side constituting a heater side and the other side functioning as sensor side. The contact pads can be screen-printed, while the contact terminals can be resistance-welded or any other suitable joining process to one or more of the contact pads. To minimize thermal loss, the substrate has a minimum contact surface with the housing and can be designed for less operating power. The sensor occupies less space as the sensor element size is minimized according to such a design. The circular ceramic substrate generally includes a platinum heater on one side (i.e., the heater side) and platinum electrodes on the other side, which provide for printing sensing material, such as a metal oxide semiconductor.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DESCRIPTION

The particular values and configurations discussed in these non-limiting examples can be varied and are cited merely to illustrate at least one embodiment and are not intended to limit the scope thereof.

Figure 1:
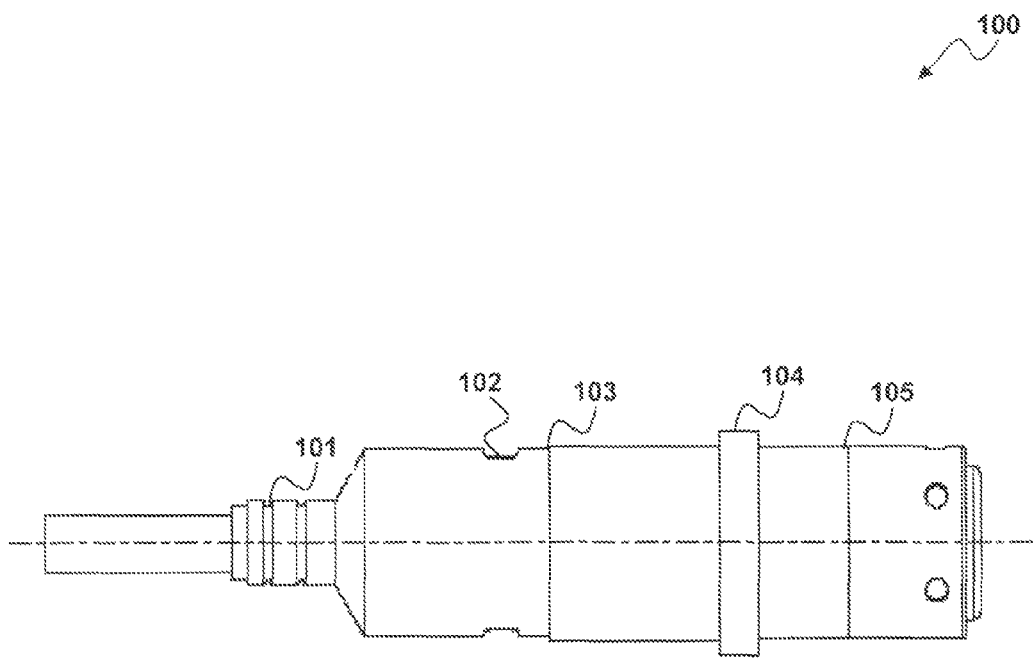
FIG. 1 illustrates a front view of gas sensor apparatus, which can be implemented in accordance with a preferred embodiment.
Figure 2A:
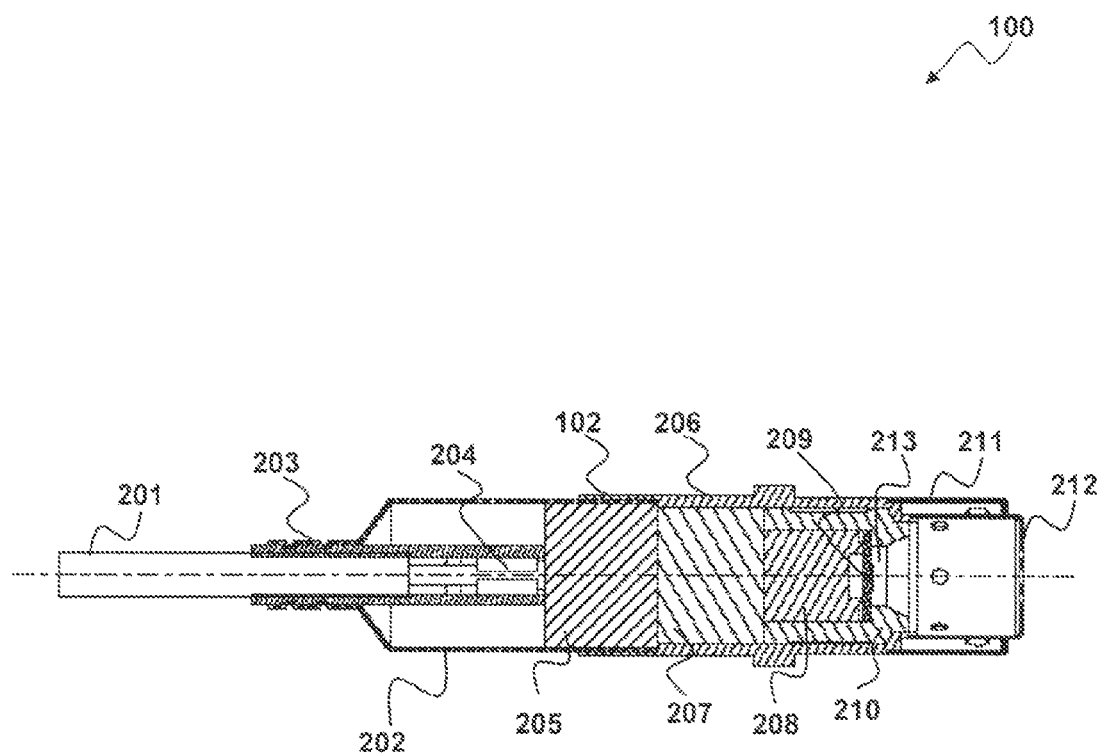
FIG. 2A illustrates a longitudinal cross-sectional view of the gas sensor apparatus depicted in FIG. 1, which can be implemented in accordance with a preferred embodiment.

FIG. 1 illustrates a side view of a gas sensor apparatus 100, which can be implemented in accordance with a preferred embodiment. FIG. 2A illustrates a longitudinal cross-sectional view of the gas sensor apparatus 100 as depicted in FIG. 1, in accordance with a preferred embodiment. The gas sensor apparatus 100 generally includes an embossing 102, a laser welding 103, a collar 104, and a welding 105. The gas sensor apparatus 100 includes a crimping 101 to seal the cable 201 as depicted in FIG. 2A, and an embossing 102 to retain a ceramic insulator 205 as also depicted in FIG. 2A and laser welding 103 of a rear cover 202 with a main shell 206 as further depicted in FIG. 2A. The gas sensor apparatus 100 also includes a collar 104 located in a portion of the main shell 206 as indicated in FIG. 2A and a welding 105 of an outer baffle 211 as depicted in FIG. 2A with the main shell 206.

The gas sensor apparatus 100 shown in FIG. 2A can be utilized to determine the gas content of exhaust gas generated by an internal combustion engine. The gas sensor apparatus 100 includes a connecting cable 201 associated with a rear cover 202, a sleeve 203 a metallic wire 214 to cable crimping 204 (shown in FIG. 2b). Note that the sleeve 203 can be formed from, for example, TEFLON. A sensor element 209 can be held by an inner ceramic holder 208 and an outer ceramic holder 210 maintained within the main shell 206. A ceramic insulator 205 and a ceramic potting 207 can also be provided. The sensor element 209 is generally surrounded by an outer baffle 211 and an inner baffle 212 in the region 213 where the sensor element 209 is exposed to the exhaust gases.

Figure 2B:
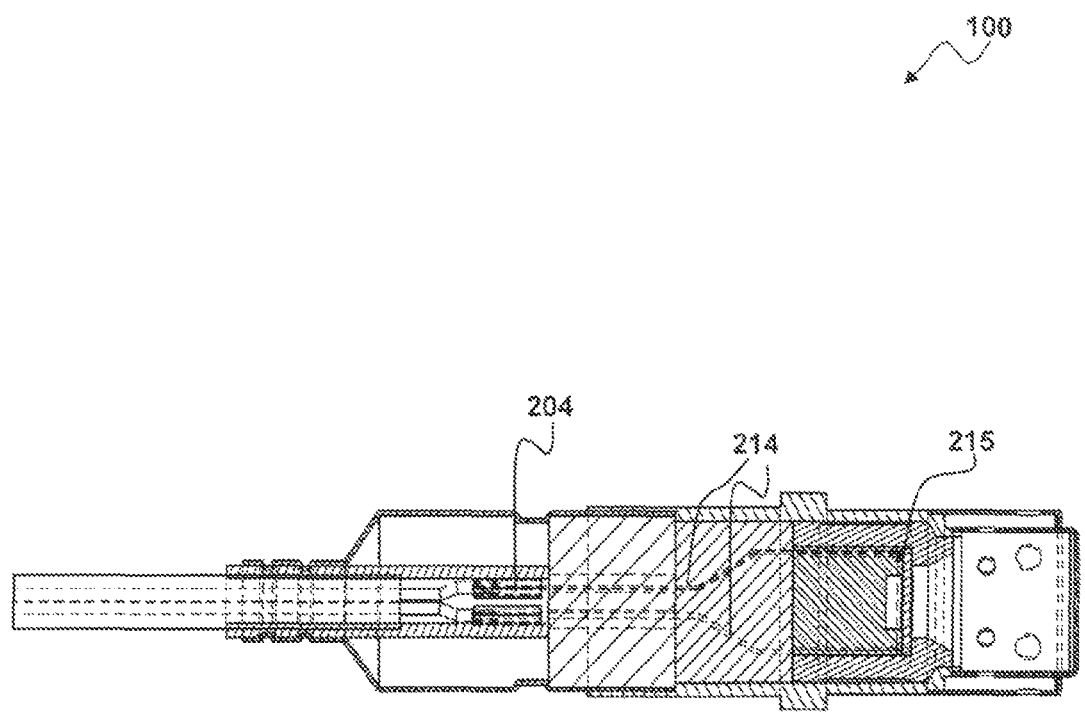
FIG. 2B illustrates a longitudinal cross-sectional view of the gas sensor apparatus depicted in FIGS. 1-2A, which can be implemented in accordance with a preferred embodiment.

FIG. 2B illustrates a longitudinal sectional view of the gas sensor apparatus 100 depicted in FIGS. 1-2A, which can be implemented in accordance with a preferred embodiment. Note that in the embodiment disclosed herein, four metallic wires 214 are indicated. It can be appreciated, however, that this number may vary; that is, fewer or more metallic wires 214 may be utilized depending upon design considerations. The longitudinal sectional view depicted in FIG. 2B of the gas sensor apparatus 100 illustrates the metallic wires 214 with cable crimping 204 and joined with substrate 215.

Figure 3:
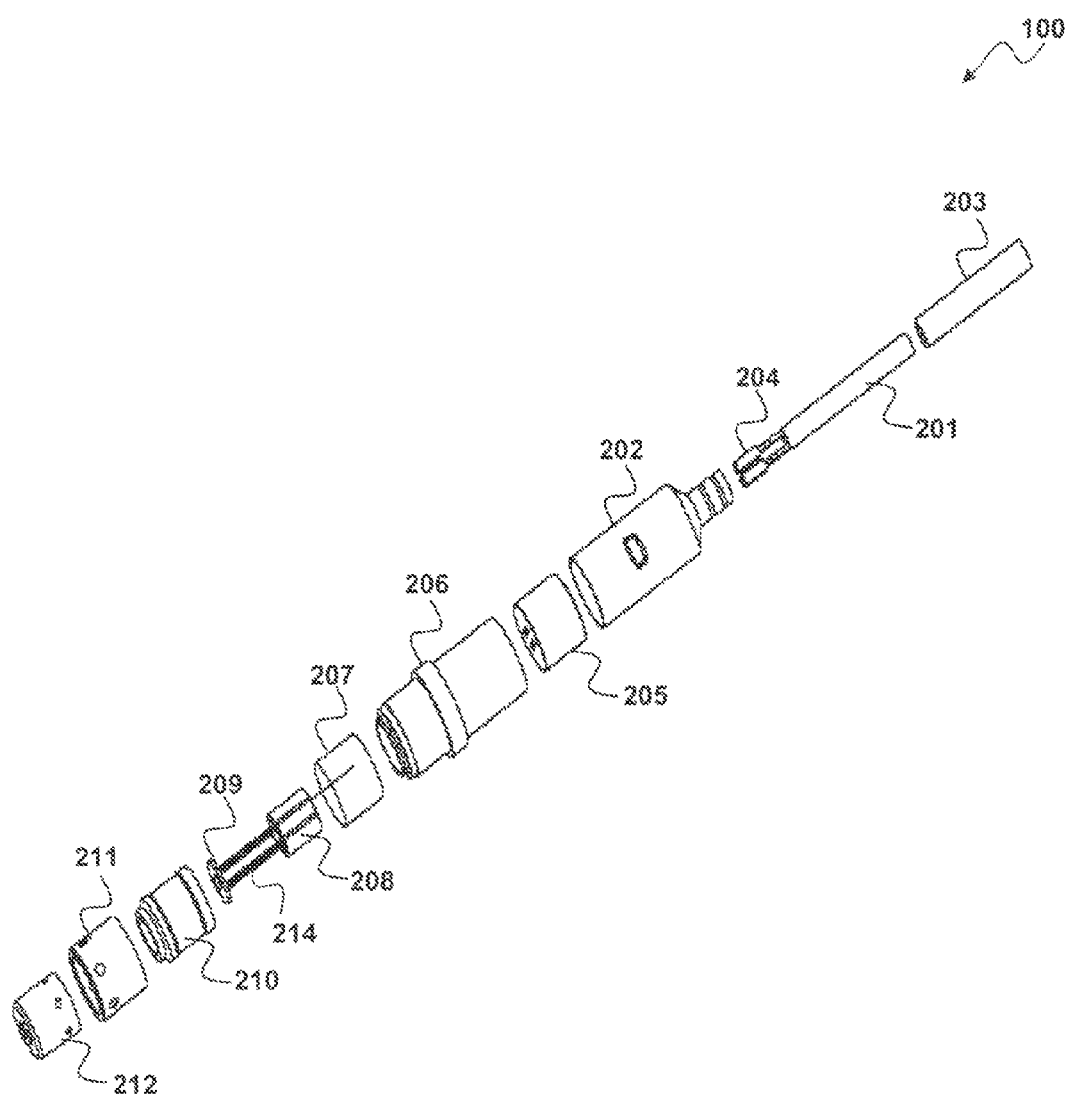
FIG. 3 illustrates exploded view of the gas sensor apparatus as depicted in FIGS. 1-2, which can be implemented in accordance with an alternative embodiment.

FIG. 3 illustrates an exploded view of the gas sensor apparatus 100, which can be implemented in accordance with an alternative embodiment. The gas sensor apparatus 100 depicted in FIG. 1 includes a TEFLON sleeve 203, a connecting cable 201, a metallic wire 214 to cable crimping 204, a rear cover 202, a ceramic insulator 205, a main shell 206, and a ceramic potting 207. The gas sensor apparatus 300 also includes a sensor element 209 with an inner ceramic holder 208 and an outer ceramic holder 210. The TEFLON sleeve 203 provides a grease-free connection to the connecting cable 201 which is tied tightly with the metallic wires 214 that are encapsulated within a rear cover 202. The outer ceramic holder 210 and inner ceramic holder 208 hold the sensor element 209 embedded within the ceramic substrate 401 as depicted in FIG. 4.

The ceramic insulator 205 and ceramic potting 207 provides thermal insulation to the sensor element 209. The gas sensor apparatus 100 additionally includes outer baffle 211 and inner baffle 212 which act as a protective shield for the sensor element 209 in a region 213 where the sensor element 209 is exposed to exhaust gases. The sensor element 209, ceramic insulator 205, ceramic potting 207, inner ceramic holder 208 and outer ceramic holder 210 are enclosed within a main shell 206 which prevents the sensor element 209 from breakage. Note that in FIGS. 2A and 3, identical or similar parts or elements are generally indicated by identical reference numerals. Thus, the reference numerals 201, 202, 203, 204, 205, 206, 207, 208, 209, 210, 211, and 212 as depicted in FIG. 2A refer to the same components in FIG. 3.

Figure 4:
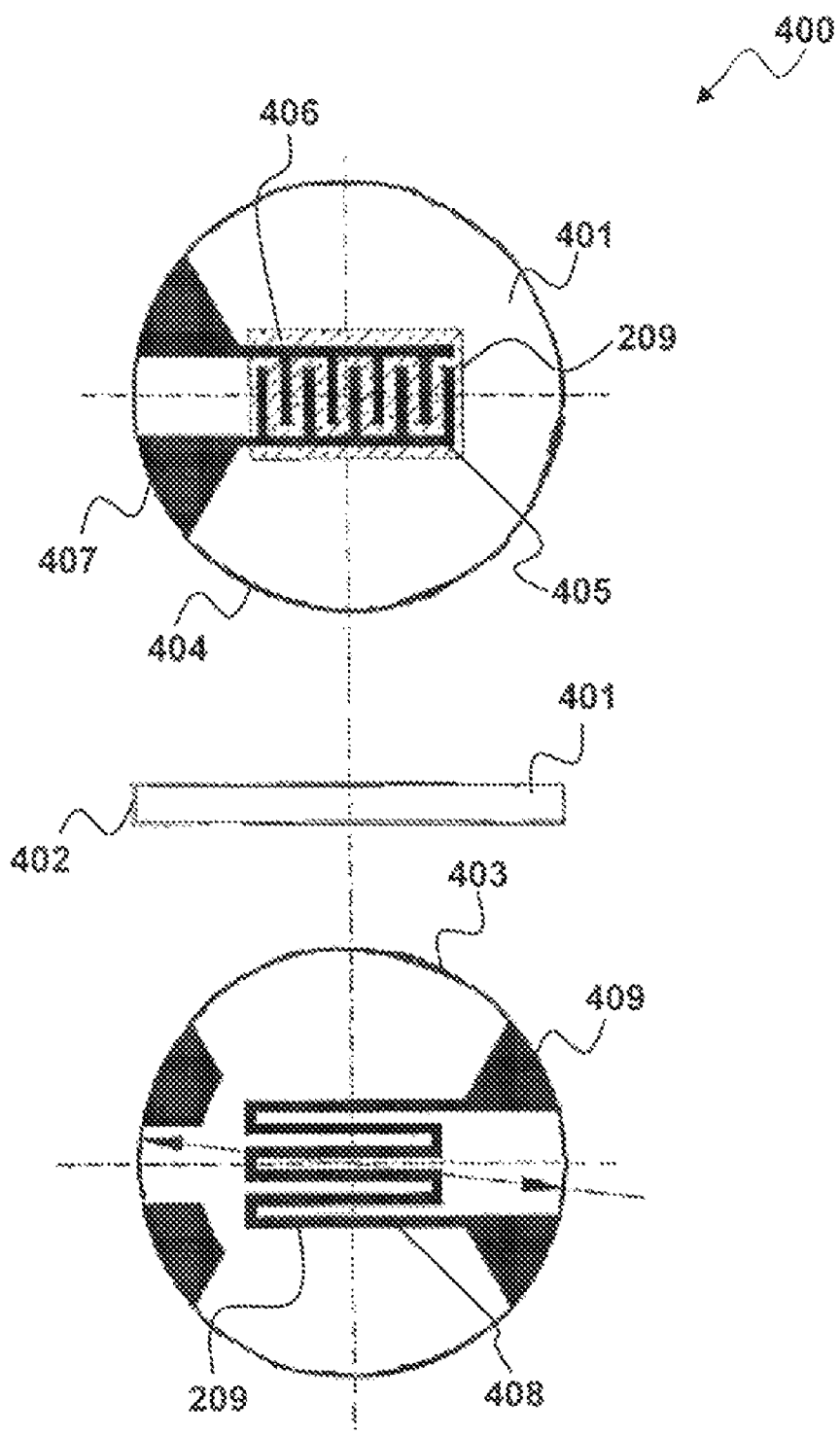
FIG. 4 illustrates a schematic drawing for top, front and bottom views of a sensor element, which can be implemented in accordance with an alternative embodiment.

FIG. 4 illustrates a schematic side view of a sensing component 400 and a sensor element 209, which can be implemented in accordance with an alternative embodiment. As indicated in FIG. 4, the sensor element 209 can be embedded in a substrate 401 having a side platinum conductive coating 402 to take the sensing electrode to the rear side. To avoid breakage of the sensor element 209, the substrate 401 can be preferably formed in a circular shape in which one side of the substrate 401 constitutes the heater side 403 and the other or opposite side of the substrate 401 functions as the sensor side 404. The substrate 401 can be configured, for example, from materials such as aluminum oxide. Sensing component 400 can be adapted for use with the gas sensor apparatus 100 described herein, depending upon design considerations.

The sensor side 404 can include a sensing material 405, which can be, for example, a metal oxide semiconductor coated via screen-printing or attaching a sensing element over the substrate. The sensor side 404 includes sensing side electrodes 406 for measuring sensor signal and platinum electrode 407 held in ceramic substrate 401. The heater side 403 generally includes a platinum heater 408 that maintains a temperature approximately >650° C. for sensor element 209 and electrodes 409 for connecting wires. The sensor element 209 can be suspended in order to minimize heat transfer between the sensor element 209 and the gas sensor packaging 100. Such a structure has the advantage that the platinum heater element 408 provides heat to the sensor element 209 over an area that results in essentially uniform, balanced thermal conditions and which counteract the tendency of the sensor element 209 to fracture.

Figure 5:
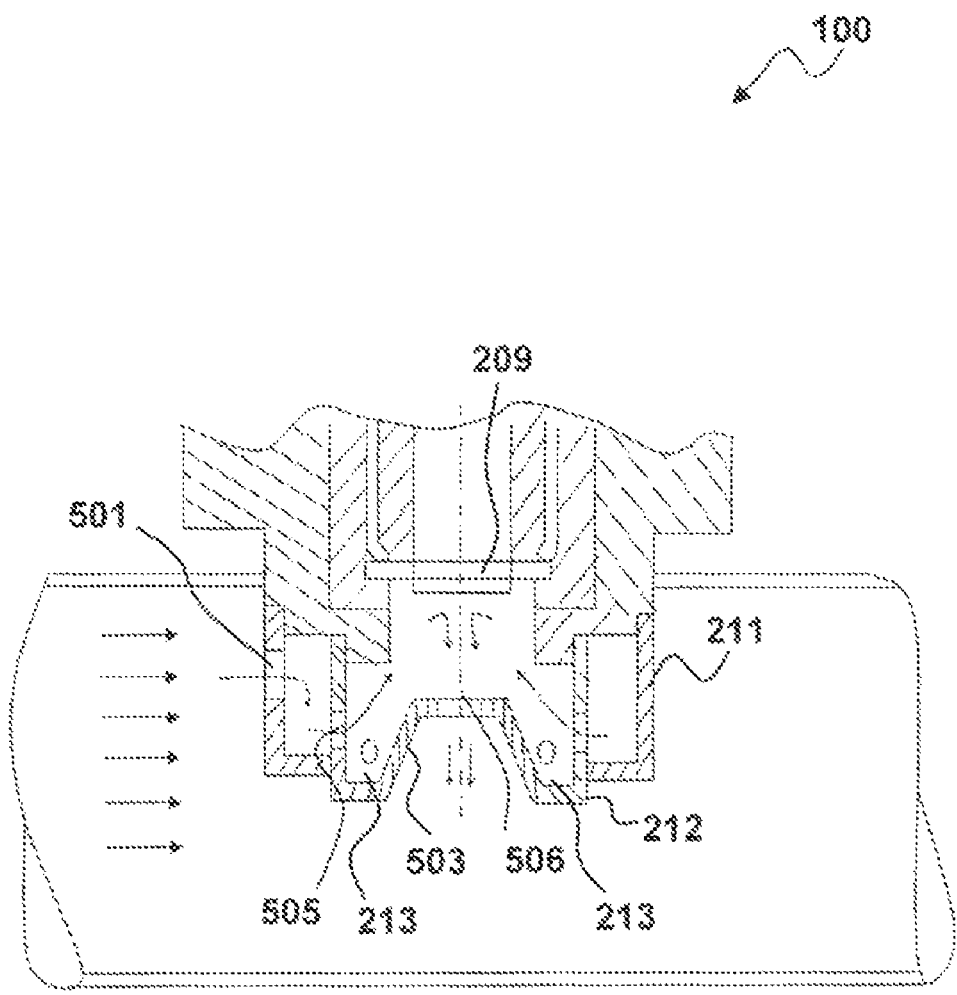
FIG. 5 illustrates a sectional view of improved gas flow of the gas sensor apparatus, which can be implemented in accordance with a preferred embodiment.

FIG. 5 illustrates a sectional view of improved gas sensor apparatus 100, including a gas flow to the sensor element 209, in accordance with a preferred embodiment. Note that in FIGS. 2 and 5 identical or similar parts or elements are generally indicated by identical reference numerals. Thus, the reference numerals 209, 211 and 212 as depicted in FIG. 2 refer to the same components in FIG. 5. The gas sensor element 209 includes a gas-exposed portion. The gas sensor apparatus 100 maintains the gas sensor element 209 and includes an outer baffle 211 and an inner baffle 212 so as to shield the gas-exposed portion of the sensing element 209. The inner baffle 212 forms a cup-like groove 213 towards the gas sensor element 209. Reference numerals 501 and 505 represent inlet holes formed in the outer and inner baffles and reference numeral 506 represents a single outlet of inner baffle. Gas enters through inlet 501 of outer baffle 211 and enters through inlets 505 of inner baffle 212. The gas flows and hits the embossed feature 503 of inner baffle 212 and flows upward to gas sensor element 209. Gas exits through outlet 506 of inner baffle.

Figure 6:
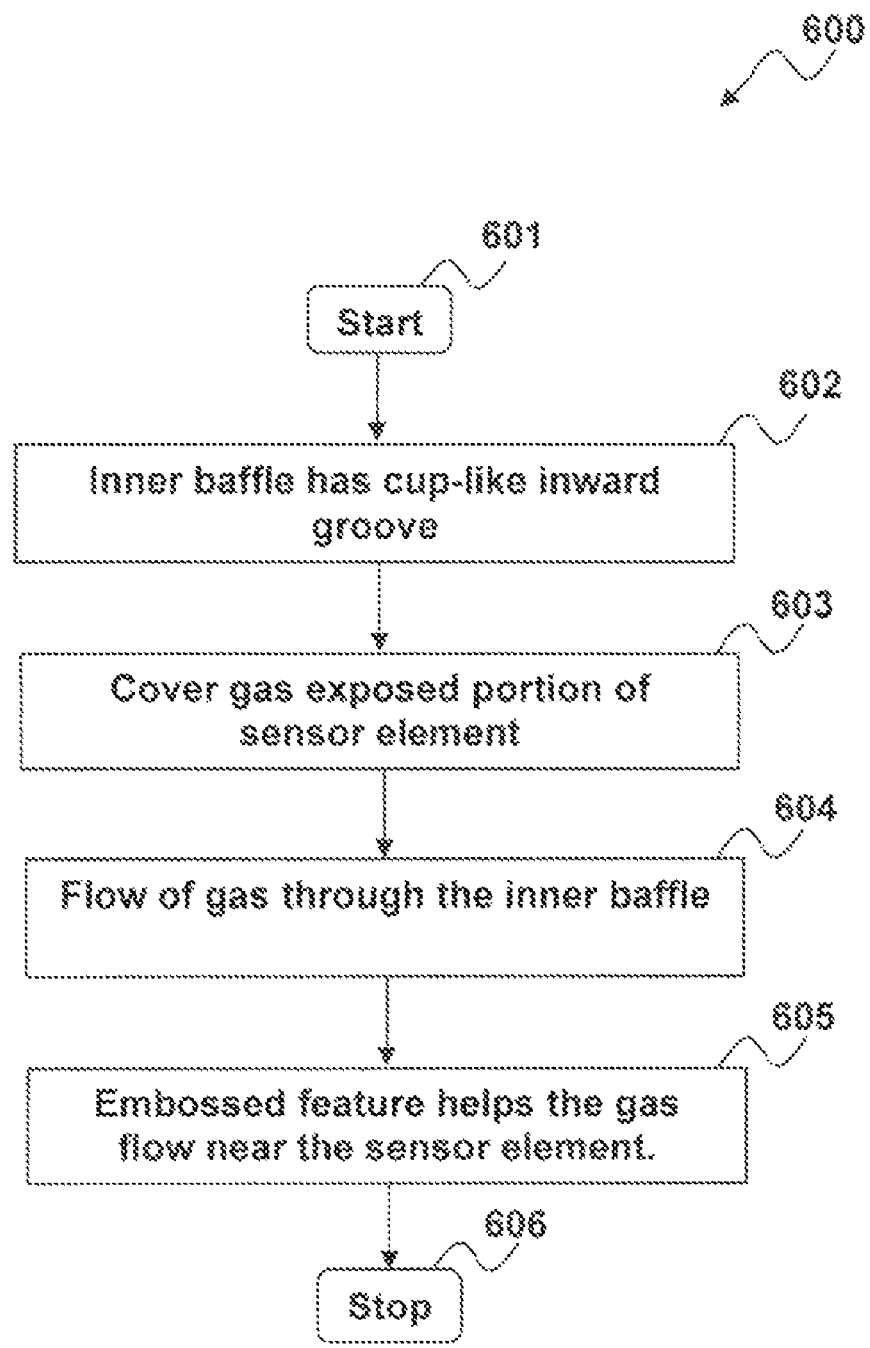
FIG. 6 illustrates a high level flow chart of operations depicting an improved method of gas flow to the sensor element, which can be implemented in accordance with a preferred embodiment.

FIG. 6 illustrates a high-level flow chart of operations depicting logical operational steps of a method 600 for forming the improved gas sensor apparatus 100, in accordance with a preferred embodiment. Note that the method 600 illustrated in FIG. 6 can be followed to construct the gas sensor apparatus described previously. As indicated at block 601, the process begins. Thereafter, as depicted at block 602, the metallic housing contains an inner baffle and an outer baffle to cover the gas exposed portion of sensor element. The inner baffle can be configured as indicated next at block 603 to contain a cup-like groove 213 (FIG. 5) extending inward. Thereafter, as depicted at block 604, the flow of gas through the inner baffle can be provided. As depicted at block 605, the embossed feature described earlier can be provided to assist the gas flow near the sensor element. The process can then terminate as indicated at block 606.

Figure 7A:
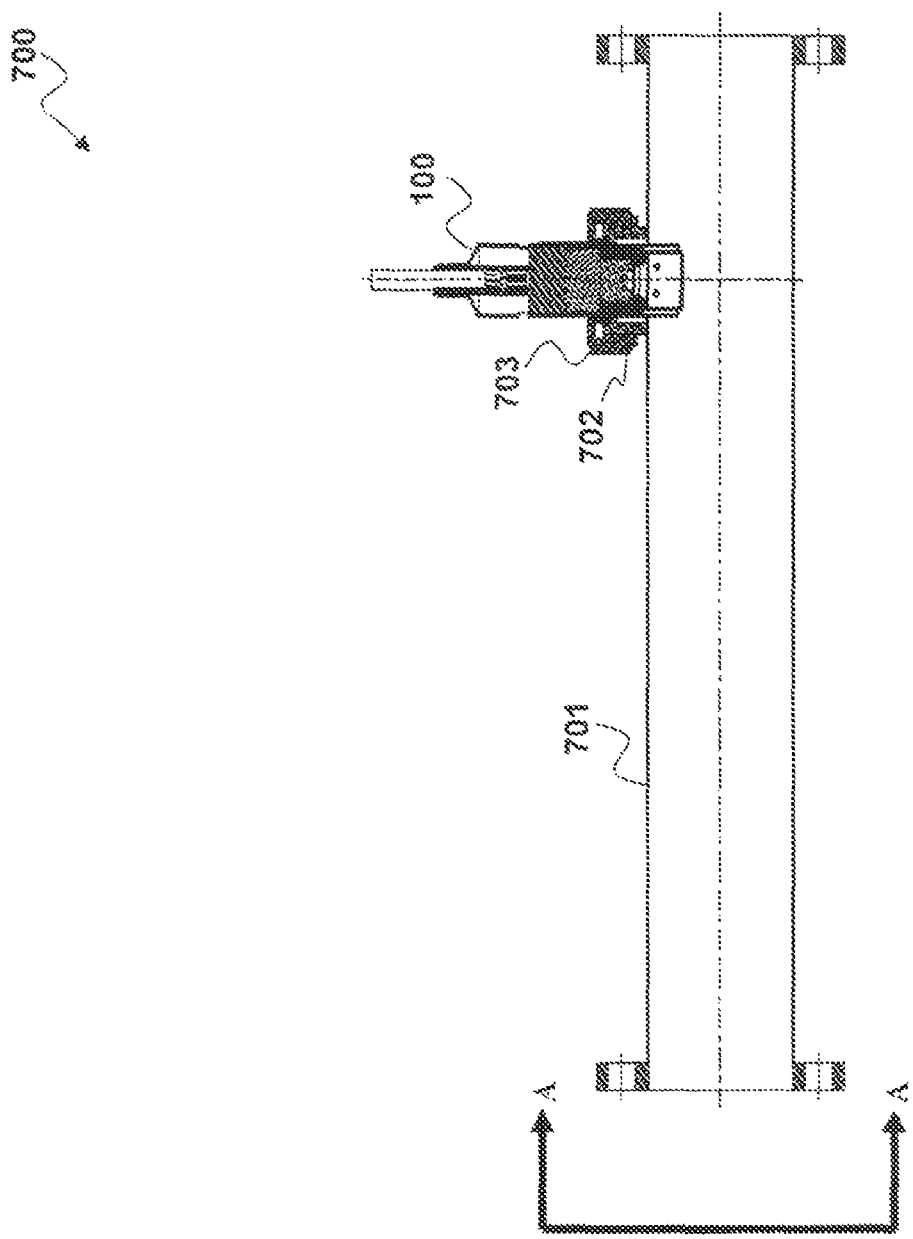
FIG. 7A illustrates a front view of a pipe-gas sensor apparatus assembly employed to determine the gas content such as NOx, O2, CO, CO2, etc., of exhaust gas generated by an internal combustion engine, which can be implemented in accordance with an alternative embodiment.

FIG. 7A illustrates a front view of a pipe-gas sensor apparatus 700 employed to determine the $NO_x$ content of exhaust gas generated by an internal combustion engine, which can be implemented in accordance with an alternative embodiment. The gas sensor apparatus 100 can be mounted on an exhaust pipe 701. The pipe holder 702 is designed to hold the gas sensor apparatus 100 on the exhaust pipe 701. An outer nut 703 of the screw joining the gas sensor apparatus 100 to the pipe holder 702 is also illustrated in the view.

Figure 7B:
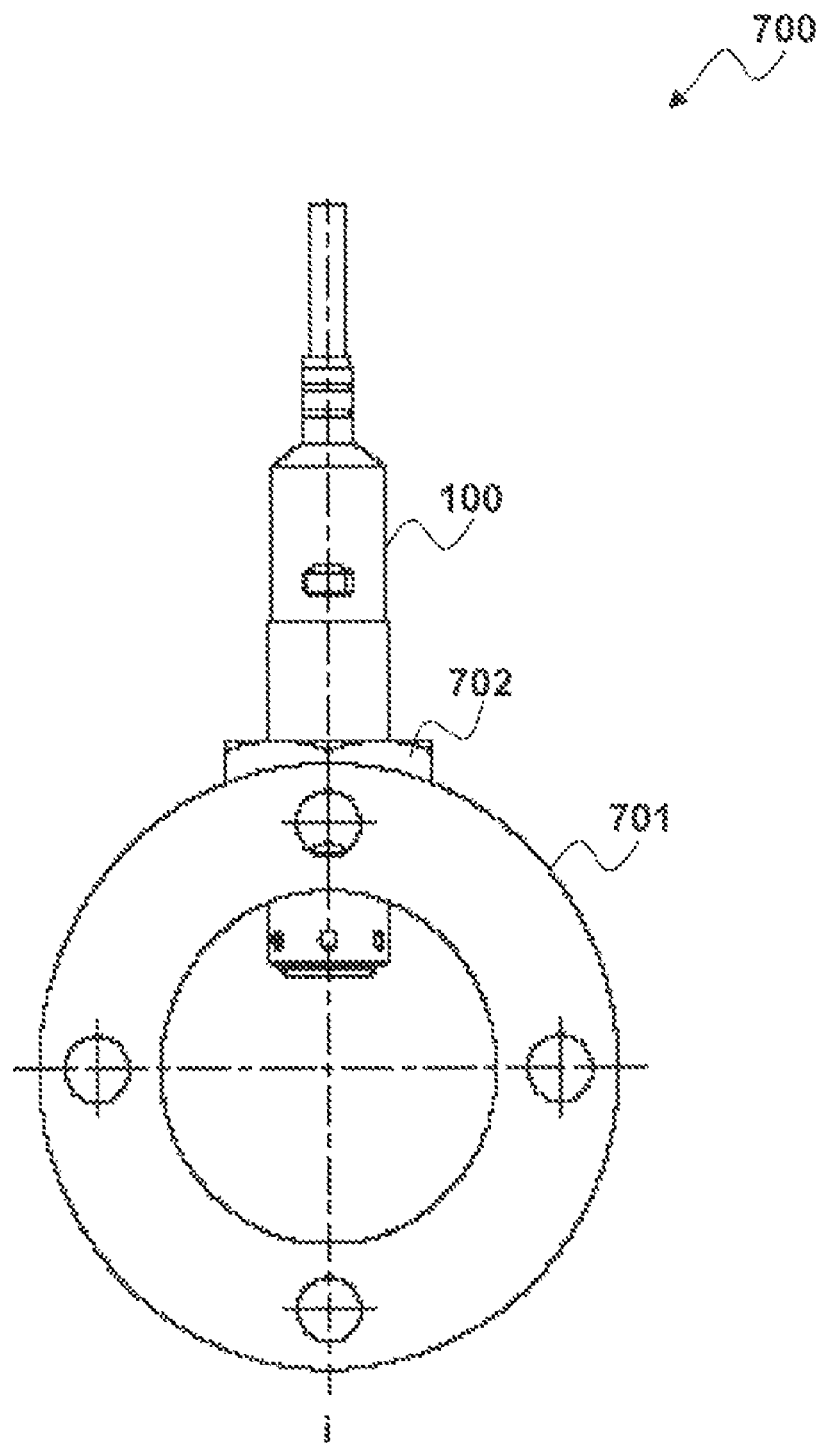
FIG. 7B illustrates a side view taken along line 7B-7B of FIG. 7A of a pipe-gas sensor assembly, which can be utilized to determine the gas content of exhaust gas generated by an internal combustion engine, which can be implemented in accordance with an alternative embodiment.

FIG. 7B illustrates a side view A 700 of pipe-gas sensor assembly, which can be utilized to determine the gas content of exhaust gas generated by an internal combustion engine, which can be implemented in accordance with an alternative embodiment. Note that in FIGS. 7A and 7B, identical or similar parts or elements are generally indicated by identical reference numerals. Thus, the reference numerals 100, 701, and 702 as depicted in FIG. 7A refer to the same components in FIG. 7B. Note that in FIGS. 1-7, identical or similar parts or elements are indicated by identical reference numerals. Thus, the FIG. 7 illustration also generally contains the gas sensor apparatus 100 which is described above with respect to FIGS. 1-7.

It will be appreciated that variations of the above-disclosed and other features and functions, or alternatives thereof, may be desirably combined into many other different systems or applications. Also, it can be appreciated that various presently unforeseen or unanticipated alternatives, modifications, variations or improvements therein may be subsequently made by those skilled in the art, which are also intended to be encompassed by the following claims.

What is claimed is:

1. An elongated gas sensor apparatus extending generally along a longitudinal axis, comprising:
    a ceramic substrate including a first major surface and a second major surface opposite the first major surface, the first and second major surfaces orientated perpendicular to the longitudinal axis of the gas sensor apparatus;
    a gas sensor element comprising a heater element supported by the first major surface of the ceramic substrate, and a plurality of electrodes supported by the second major surface of the ceramic substrate, wherein at least some of the plurality of electrodes supported by the second major surface of the ceramic substrate are in contact with a sensing material, wherein the sensing material is a different material than the ceramic substrate; and
    a metallic housing surrounding said gas sensor element, the metallic housing comprising an outer baffle and an inner baffle, wherein the inner baffle is shaped to direct a flow of exhaust gas towards said gas sensor element.

2. The apparatus of claim 1, wherein said ceramic substrate has a substantially circular shape in order to prevent a breakage of said gas sensor element, avoid thermal loss, and permit said gas sensor apparatus to withstand mechanical shock and vibrations while occupying a minimal package space.

3. The apparatus of claim 1 further comprising:
    a plurality of contact terminals connected to said ceramic substrate in order to provide at least one electrical connection to the gas sensor element.

4. The apparatus of claim 3 wherein the outer baffle and the inner baffle are configured such that they cover a gas exposed portion of said gas sensor element.

5. The apparatus of claim 1 wherein said gas sensor element comprises a holding end portion located and secured in said metallic housing, and a sensing end portion exposed to an exhaust gas stream of an engine.

6. The apparatus of claim 1 wherein said heater element comprises a plurality of platinum heater elements, and said plurality of electrodes comprises platinum.

7. The apparatus of claim 1 wherein the plurality of electrodes are coated with the sensing material.

8. The apparatus of claim 1 wherein said gas sensor element comprises at least one platinum conductive pad and a plurality of contact terminals, wherein said plurality of contact terminals are resistance-welded to said ceramic substrate.

9. The apparatus of claim 1 wherein said heater element maintains a temperature of said gas sensor element.

10. The apparatus of claim 1, the metallic housing further comprising an embossed element that assists the flow of exhaust gas toward said gas sensor element.

11. A method of forming an elongated gas sensor apparatus extending generally along a longitudinal axis, comprising:
providing a gas sensor element including a ceramic substrate having a first major surface and a second opposing major surface, the first and second major surfaces oriented perpendicular to the longitudinal axis of the gas sensor apparatus, a heater element disposed on the first major surface of the ceramic substrate, and a plurality of electrodes disposed on the second major surface of the ceramic substrate, wherein said heater element maintains a temperature of said gas sensor element;
disposing a sensing material on at least some of the plurality of electrodes, wherein the sensing material is a different material than the ceramic substrate;
positioning said gas sensor element in a metallic housing such that the gas sensor element including the heater element and the ceramic substrate are surrounded and protected by the metallic housing;
said metallic housing having an outer baffle and an inner baffle so as to cover a gas exposed portion of said gas sensor element;
said inner baffle is shaped to direct a flow of exhaust gas towards said gas sensor element; and
wherein said ceramic substrate is configured to be substantially circular in shape to help prevent a breakage of said gas sensor element, avoid thermal loss, and permit said gas sensor apparatus to withstand mechanical shock and vibrations while occupying a minimal package space.

12. The method of claim 11 further comprising:
connecting a plurality of contact terminals to said ceramic substrate to provide at least one electrical connection to said gas sensor.

13. The method of claim 11 further comprising:
configuring said gas sensor element to comprise a holding end portion located and secured in said metallic housing and a sensing end portion exposed to exhaust gases.

14. The method of claim 11 further comprising:
configuring said gas sensor element to comprise at least one platinum conductive pad;
resistance-welding a plurality of contact terminals to said ceramic substrate;
and
providing an embossed element that assists the flow of exhaust gas near said gas sensor element.

15. A gas sensor apparatus extending along a longitudinal axis, comprising:
a ceramic substrate including a first major surface and a second major surface opposite the first major surface, the first and second major surfaces of the ceramic substrate orientated substantially perpendicular to the longitudinal axis of the gas sensor apparatus;
a gas sensor element comprising a heater element supported by the first major surface of the ceramic substrate and a plurality of electrodes supported by the second major surface of the ceramic substrate, wherein at least some of the plurality of electrodes are in contact with a sensing material, wherein the sensing material is a different material than the ceramic substrate; and
a metallic housing supporting the gas sensor element, the metallic housing comprising an outer baffle and an inner baffle, wherein the outer baffle directs a flow of exhaust gas from a direction substantially perpendicular to the longitudinal axis of the gas sensor apparatus towards the inner baffle, and the inner baffle directs the flow of exhaust gas towards the sensing material and the plurality of electrodes on the second major surface of the ceramic substrate of the gas sensor element, the inner baffle also having an outlet that channels the flow of exhaust gas out of the metallic housing.

* * * * *